United States Patent [19]

Ensminger et al.

[11] 4,143,141

[45] Mar. 6, 1979

[54] METHOD OF TREATING ACNE WITH ANTIBIOTIC A201A

[75] Inventors: Paul W. Ensminger, Indianapolis; Robert L. Hamill, Greenwood, both of Ind.

[73] Assignee: Eli Lilly and Company, Indianapolis, Ind.

[21] Appl. No.: 833,127

[22] Filed: Sep. 14, 1977

[51] Int. Cl.$^2$ .............................................. A61K 31/52
[52] U.S. Cl. ................................... 424/253; 424/119; 424/122
[58] Field of Search ................................. 424/119, 253

[56] References Cited

U.S. PATENT DOCUMENTS 3,843,784  10/1974  Hamill et al. .................. 424/119

OTHER PUBLICATIONS

Happonen, Handbook of Non-Prescription Drugs, 5th ed., pp. 316–320, Jan. 1977.
Fulton et al., Arch. Dermatol., 110, pp. 83–86 (1974).

*Primary Examiner*—Leonard Schenkman
*Attorney, Agent, or Firm*—Nancy J. Harrison; Arthur R. Whale

[57] ABSTRACT

A method for the topical treatment of acne with antibiotic A-201A and A-201A compositions for acne are disclosed.

6 Claims, No Drawings

METHOD OF TREATING ACNE WITH ANTIBIOTIC A201A

BACKGROUND OF THE INVENTION

1. Field of the Invention

The invention relates to the topical treatment of acne. Acne is a common inflammatory disease involving sebaceous glands. Acne generally appears in early adolescence, affecting more than 80% of teenagers. The severity of the inflammation varies. It is characterized, in order of increasing severity, by comedones, pustules, papules, inflamed nodules, infected cysts, and, in extreme cases, canalizing inflamed and infected sacs.

*Corynebacterium acnes* and *Staphylococcus aureus*, normally found in the flora of the skin, have been implicated as contributing agents in the more inflammatory types of acne. It is believed that *C. acnes* splits the triglycerides in the sebum, thereby liberating free fatty acids and causing the inflammation of acne.

The currently accepted name for *Corynebacterium acnes*, *Propionibacterium acnes*, will be used in the specification in discussions of the activity of antibiotic A-201A.

2. The Prior Art

A variety of treatments have been used for acne. Topical antibacterials, such as hexachlorophene, retinoic acid and corticosteroid lotions, with or without neomycin, have been used with moderate success. Systemic administration of broad-spectrum antibiotics, such as tetracycline and clindamycin, may improve severe acne, but the risk of side effects is great. Neither systemic antibiotic therapy nor topical treatments have, therefore, been satisfactory remedies for acne.

Generally, antibiotics have not been used in the topical treatment of acne. Exceptions include the use of neomycin, erythromycin, and antibiotics of the lincomycin family, such as clindamycin (U.S. Pat. No. 3,969,516). We have now discovered that antibiotic A-201A is an effective agent for the topical treatment of acne. Antibiotic A-201A is described by Hamill et al. in U.S. Pat. No. 3,843,784. The structure of A-201A has been determined by H. A. Kirst et al., (ICAAC Meeting, Chicago, Ill., October, 1976) to be as follows:

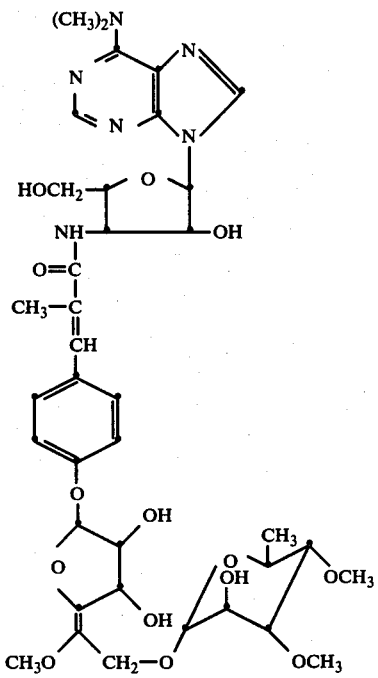

SUMMARY OF THE INVENTION

We have discovered that antibiotic A-201A is useful in the topical treatment of acne. This invention relates, therefore, to a method for alleviating the symptoms of acne by topically administering an effective amount of a composition containing from about 0.1 to about 10 percent by weight of antibiotic A-201A. This invention further relates to compositions for the treatment of acne comprising from about 0.1 to about 10 percent by weight of antibiotic A-201A and suitable pharmaceutical formulating agents.

DETAILED DESCRIPTION OF THE INVENTION

This invention relates to a method for treating acne which comprises topically administering to a human suffering from acne an effective amount of a composition containing from about 0.1 to about 10 percent by weight of antibiotic A-201A. This invention further relates to compositions for the treatment of acne which comprise from about 0.1 to about 10 percent by weight of antibiotic A-201A together with a suitable pharmaceutical formulating agent or agents.

U.S. Pat. No. 3,843,784 describes antibiotic A-201A and the method by which it is prepared by cultivation of the organism *Streptomyces capreolus* NRRL 3817. The *S. capreolus* strain by which antibiotic A-201A may be prepared is available from the Northern Regional Research Laboratory, Agricultural Research Service, U.S. Department of Agriculture, 1815 North University Street, Peoria, Ill. 61604 under the accession number NRRL 3817.

When antibiotic A-201A is used for the treatment of acne, it is applied topically in a composition comprising from about 0.1 to about 10 percent of A-201A by weight. It is preferable to apply A-201A in a composition containing from about 0.1 to about 5 percent of A-201A by weight. An especially preferred composition contains from about 1 to about 3 percent of A-201A by weight. The term "an effective amount of the composition", as used herein, refers to an amount which is effective in the therapeutic treatment of acne.

In the treatment of acne, A-201A compositions are generally applied several times daily in conventional amounts. Conventional amounts are amounts which are sufficient to thinly spread the composition over the affected area. Treatments are continued until the acne has disappeared. Antibiotic A-201A is relatively non-toxic. The intravenous $LD_{50}$ of A-201A in rats, for example, is approximately 2,000 mg/kg. This characteristic (low toxicity) of A-201A makes it especially valuable when used in the treatment of acne.

This invention further relates to compositions for the treatment of acne comprising from about 0.1 to about 10 percent of antibiotic A-201A by weight together with a suitable pharmaceutical formulating agent. Preferred A-201A compositions contain from about 0.1 to about 5 percent A-201A by weight, and especially preferred compositions contain from about 1 to about 3 percent A-201A by weight. Typical compositions comprise antibiotic A-201A dissolved in a suitable topical formulation, for example, a gel, cream, lotion, spray, or solution. The remaining ingredients in an A-201A composition may be any of the conventional formulating ingredients, such as, for example, ethyl alcohol, isopropyl alcohol, acetone, polyvinylpyrrolidone, propylene glycol, fragrances, gel-producing materials, water, benzyl alcohol, stearyl alcohol, stearic acid, sorbitan monooleate, Polysorbate 80, sorbital solutions, methylcellulose, sodium citrate, and sodium lauryl sulfate.

Additional ingredients include from 0 to 50 percent polyethylene glycol (200, 300, 400, 600, etc.); from 0 to 5 percent of a surfactant such as Tween 80; from 0 to 10 percent of a penetrating agent, such as urea or an alkyl methyl sulfoxide; and from 0.5 to 2 percent of a stabilizing agent, such as a chelating agent, buffer, antioxidant, etc.

The activity of antibiotic A-201A against *Staphlococcus aureus* was described in U.S. Pat. No. 3,843,784. Table I shows that A-201A is also active against *Propionibacterium acnes*, the anaerobic organism most commonly associated with acne. Activity was measured using the agar-dilution test described by V. L. Sutter et al. in *Applied Microbiology* 23, 268–275 (1972).

| Propionibacterium acnes Strain No. | Minimal Inhibitory Concentration of A-201A (mcg/ml)* |
|---|---|
| 44 | 0.5 |
| 79 | 1.0 |
| 101 | ≦0.125 |
| 103 | ≦0.125 |
| 104 | ≦0.125 |
| 105 | ≦0.125 |
| 106 | 0.25 |
| 107 | ≦0.125 |
| 108 | ≦0.125 |

*Determined after 24-hours incubation.

The activity of antibiotic A-201A against other representative anaerobic bacterial isolates, using the above-described agar-dilution test, is summarized in Table II.

Table II

| Anaerobic Bacteria | Minimal Inhibitory Concentration of A-201A (mcg/ml)* |
|---|---|
| *Actinomyces israelii* W855 | ≦0.5 |
| *Clostridium perfringens* 81 | 1.0 |
| *Clostridium septicum* 1128 | ≦0.5 |
| *Eubacterium aerofaciens* 1235 | ≦0.5 |

Table II-continued

| Anaerobic Bacteria | Minimal Inhibitory Concentration of A-201A (mcg/ml)* |
|---|---|
| *Peptococcus asaccharolyticus* 1302 | ≦0.5 |
| *Peptococcus prevoti* 1281 | 1.0 |
| *Peptostreptococcus anaerobius* 1428 | ≦0.5 |
| *Peptostreptococcus intermedius* 1264 | 2 |
| *Propionibacterium acnes* 79 | 2 |
| *Bacteroides fragilis* 111 | <128 |
| *Bacteroides fragilis* 1877 | 16 |
| *Bacteroides fragilis* 1936B | 16 |
| *Bacteroides thetaiotaomicron* 1438 | 8 |
| *Bacteroides melaninogenicus* 1856/28 | 4 |
| *Bacteroides melaninogenicus* 2736 | 8 |
| *Bacteroides vulgatis* 1211 | 8 |
| *Bacteroides corrodens* 1874 | 8 |
| *Fusobacterium symbiosum* 1470 | ≦0.5 |
| *Fusobacterium necrophorum* 6054 A | 2 |

The susceptibility of a number of anaerobic cocci isolates to antibiotic A-201A is shown in Table III. Activity was measured, using the above-described agar-dilution test, after 24-hr. incubation.

Table III

| Anaerobic Coccus | Minimal Inhibitory Concentration of A-201A (mcg/ml)* |
|---|---|
| *Peptococcus asaccharolyticus* 1302 | 0.5 |
| *Peptococcus asaccharolyticus* 1344 | <0.06 |
| *Peptococcus constellatus* 1468 | 4 |
| *Peptococcus magnus* 1401 | <0.06 |
| *Peptococcus magnus* 1421 | 1.0 |
| *Peptococcus magnus* 1477 | 1.0 |
| *Peptococcus prevoti* 1281 | 0.125 |
| *Peptococcus prevoti* 1293 | 0.5 |
| *Peptococcus prevoti* 1407 | 0.125 |
| *Peptostreptococcus anaerobius* 8 | <0.06 |
| *Peptostreptococcus anaerobius* 52 | 0.125 |
| *Peptostreptococcus anaerobius* 59 | <0.06 |
| *Peptostreptococcus anaerobius* 1418 | <0.06 |
| *Peptostreptococcus anaerobius* 1451 | 0.25 |
| *Peptostreptococcus anaerobius* 1428 | 0.25 |
| *Peptostreptococcus anaerobius* 1477 | <0.06 |
| *Peptostreptococcus intermedius* 1264 | 1.0 |
| *Peptostreptococcus intermedius* 1524 | 0.25 |
| *Peptostreptoccus intermedius* 1624 | 0.5 |

The following specific examples are provided to illustrate this invention.

EXAMPLE 1

A-201A Gel for Acne

A gel formulation of the following percentage composition is prepared.

| Ingredient | Preferred Percent (w/w) | Range Percent (w/w) |
|---|---|---|
| Antibiotic A-201A | 2.0 | 0.1–5 |
| Ethyl alcohol (95%) | 30.0 | 0–80 |
| Propylene glycol | 5.0 | 0–50 |
| Sodium lauryl sulfate | 0.2 | 0–1 |
| Sodium citrate | 0.1 | 0–1 |
| Benzyl alcohol | 2.0 | 0–5 |
| Carbomer* | 1.0 | 0.1–2 |
| Sodium hydroxide (1N) | q.s. gel | |
| Deionized water | q.s. to 100 | |

*a carboxyvinylpolymer, Carbopol 940, B. G. Goodrich Co.

EXAMPLE 2

An A-201A solution for acne is prepared as follows:

| Ingredient | Preferred Percent | Range Percent (w/v) |
|---|---|---|
| Antibiotic A-201A | 2 w/v | 0.1–5.0 |
| Ethyl alcohol | 70 w/v | 0–99.9 |

-continued

| Ingredient | Preferred Percent | Range Percent (w/v) |
| --- | --- | --- |
| Propylene glycol | q.s. 100 ml | 0–99.9 |

We claim:

1. A method for treating acne comprising topically administering to humans suffering from acne an effective amount of a composition comprising from about 0.1 to about 10 percent of antibiotic A-201A by weight.

2. The method of claim 1 wherein the composition contains from about 0.1 to about 5 percent of antibiotic A-201A by weight.

3. The method of claim 1 wherein the composition contains from about 1 to about 3 percent antibiotic A-201A by weight.

4. A topical composition for the treatment of acne in the form of a gel, cream or lotion comprising pharmaceutical formulating agents and from about 0.1 to about 10 percent of antibiotic A-201A by weight.

5. The composition of claim 4 which contains from about 0.1 to about 5 percent of antibiotic A-201A by weight.

6. The composition of claim 5 which contains from about 1 to about 3 percent of antibiotic A-201A by weight.

* * * * *